US006316232B1

United States Patent
Sprenger et al.

(10) Patent No.: US 6,316,232 B1
(45) Date of Patent: Nov. 13, 2001

(54) MICROBIAL PREPARATION OF SUBSTANCES FROM AROMATIC METABOLISM/I

(75) Inventors: Georg Sprenger, Jülich; Ruth Siewe, Karlsruhe; Hermann Sahm, Jülich, all of (DE); Martin Karutz, Roden; Theodorus Sonke, Sittard, both of (NL)

(73) Assignees: Holland Sweetener Company V.O.F., Geleen (NL); Forschungszentrum Julich GmbH; DSM Biotech GmbH, both of Julich (DE)

( * ) Notice: Subject to any disclaimer, the term of this patent is extended or adjusted under 35 U.S.C. 154(b) by 0 days.

(21) Appl. No.: 09/298,843

(22) Filed: Apr. 26, 1999

Related U.S. Application Data

(63) Continuation of application No. PCT/NL97/00582, filed on Oct. 17, 1997.

(30) Foreign Application Priority Data

Oct. 26, 1996 (DE) .............................. 196 44 566

(51) Int. Cl.⁷ ............................ C12P 13/04; C12P 13/22; C12P 7/22; C12P 7/04
(52) U.S. Cl. ........................ 435/156; 435/106; 435/155; 435/183; 435/108
(58) Field of Search .................................. 435/183, 106, 435/108, 155, 156; 536/23.2

(56) References Cited

U.S. PATENT DOCUMENTS 5,168,056  12/1992  Frost et al. ....................... 435/172.3

FOREIGN PATENT DOCUMENTS

| 077196 | 4/1983 | (EP) . |
| 138526 | 4/1985 | (EP) . |
| 145156 | 6/1985 | (EP) . |
| 2053906 | 2/1981 | (GB) . |
| 19037/1976 | 2/1976 | (JP) . |
| 39517/1978 | 4/1978 | (JP) . |
| 96/34961 | 11/1996 | (WO) . |

OTHER PUBLICATIONS

Liao J.C. et al., "Pathway analysis, engineering, and physiological considerations for redirecting central metabolism" Biotechnology and Bioengineering, vol. 52, No. 1, Oct. 5, 1996, pp. 129–140.

Frost J.W. and Drathis K.M., "Biocatalytic syntheses of aromatics from D–glucose: renewable microbial sources of aromatic compounds", Annual Review of Microbiology, vol. 49, 1995, pp. 557–579.

Sprenger G.A. et al., "Transaldolase B of Escherichia coli K–12: cloning of its gene, talB, and characterization of the enzyme from recombinant strains" Journal of Bacteriology, vol. 177, No. 20, Oct. 1995, pp. 5930–5936.

Lu J. –L. and Liao J.C., "Metabolic engineering and control anaylsis for production of aromatics: role of transaldolase" Biotechnology and Bioengineering, vol. 53, No. 2, Jan. 20, 1997, pp. 132–138.

Zhang M. et al., "Metabolic Engineering of a Pentose Metabolism Pathway in Ethanologenic Zymomonas Mobilis", Science, vol. 267, Jan. 13, 1995, pp. 240–243.

Walfridsson M. et al., "Xylose–metabolizing Saccharomyces cerevisiae strains overexpressing the tkl1 and tal1 genes encoding the pentose phosphate pathway enzymes transketolase and transaldolase" Applied and Environmental Microbiology, vol. 61, No. 12, Dec. 1995, pp. 4184–4190.

Berry A., "Improving Production of Aromatic Compounds in Escherichia coli by metabolic engineering" Trends in Biotechnology, vol. 14, No. 7, Jul. 1996, pp. 250–256.

Gosset G. et al., "A direct comparison of approaches for increasing carbon flow to aromatic biosynthesis in Escherichia coli" Journal of Industrial Microbiology, vol. 17, No. 1, Jul. 1996, pp. 47–52.

Weisser P. et al., "Functional expression of the glucose transporter of Zymomonas mobilis leads to restoration of glucose and fructose uptake in Escherichia coli mutants and provides evidence for its facilitator action", Journal of Bacteriology, vol. 177, No. 11, Jun. 1995, pp. 3351–3354.

Primary Examiner—Rebecca E. Prouty
Assistant Examiner—Manjunath Rao
(74) Attorney, Agent, or Firm—Pillsbury Winthrop LLP

(57) ABSTRACT

The invention makes available, by means of an increased provision of intracellular metabolic intermediates, in particular of erythrose 4-phosphate, alternative processes for the microbial preparation of substances, in particular of aromatic amino acids such as L-phenylalanine, in which processes the activity of a transaldolase is increased in a microorganism producing these substances. In preferred embodiments of the invention, the activity of a transketolase or the activity of a transport protein for the PEP-independent uptake of a sugar and/or the activity of a kinase which phosporylates the relevant sugar are/is additionally increased. The invention also relates to gene structures, and to transformed cells carrying these gene structures, which make it possible to implement these processes in a particularly successful manner.

26 Claims, No Drawings

MICROBIAL PREPARATION OF SUBSTANCES FROM AROMATIC METABOLISM/I

This is a Continuation of International Appln. No. PCT/NL97/00582 filed Oct. 17, 1997 which designated the U.S.

The invention relates to a process for the microbial preparation of substances, in particular aromatic amino acids.

Microbially prepared substances, such as fine chemicals, in particular aromatic amino acids, are of great economic interest, with the requirement for amino acids, for example, continuing to increase. Thus, L-phenylalanine, for example, is used for preparing medicaments and, in particular, also in the preparation of the sweetener aspartame (α-L-aspartyl-L-phenylalanine methyl ester). L-tryptophan is required as a medicament and as an additive to animal feeds; there is likewise a need for L-tyrosine as a medicament and also as a raw material in the pharmaceutical industry. In addition to isolation from natural materials, biotechnological preparation is a very important method for obtaining amino acids in the desired optically active form under economically justifiable conditions. Biotechnological preparation is effected either using enzymes or using microorganisms. The latter, microbial, preparation enjoys the advantage that simple and inexpensive raw materials can be employed. Since the biosynthesis of amino acids in the cell is controlled in a wide variety of ways, however, a large number of attempts have already been made to increase product formation. Thus, amino acid analogues, for example, have been employed in order to switch off the regulation of biosynthesis. For example, mutants of *Escherichia coli* permitting an increased production of L-phenylalanine were obtained by selecting for resistance to phenylalanine analogues (GB-2,053,906). A similar strategy also led to overproducing strains of Corynebacterium (JP-19037/1976 and JP-39517/1978) and Bacillus (EP-0,138,526). Furthermore, microorganisms which have been constructed using recombinant DNA techniques are known in which the regulation of biosynthesis is likewise abolished, with the genes which encode key enzymes which are no longer subject to feedback inhibition being cloned and expressed. As a prototype, EP-0,077,196 describes a process for producing aromatic amino acids in which a 3-deoxy-D-arabinoheptulosonate-7-phosphate synthase (DAHP synthase) which is no longer subject to feedback inhibition is overexpressed in *E. coli*. EP-0,145,156 describes an *E. coli* strain in which chorismate mutase/prephenate dehydratase are additionally overexpressed for the purpose of producing L-phenylalanine.

A feature common to the abovementioned strategies is that the intervention for improving production is restricted to the biosynthesis pathway which is specific for the aromatic amino acids. However, in order to increase production still further, efforts must be made to improve the provision of the primary metabolites, phosphoenolpyruvate (PEP) and erythrose 4-phosphate (Ery4P), which are required for producing aromatic amino acids.

PEP is an activated precursor of the glycolysis product pyruvate; Ery4P is an intermediate in the pentose phosphate pathway.

Various attempts have been made to achieve a specific improvement in the provision of the said primary metabolite Ery4P. An increased flow of carbon through the pentose phosphate pathway was achieved in *E. coli* by switching off the enzyme phosphoglucose isomerase; this resulted in tryptophan being formed (Mascarenhas D. et al., Appl. Environ. Microbiol. 57 (1991) 2995–99). U.S. Pat. No. 5,168,056 disclosed that overexpression of a transketolase, achieved by means of recombinant DNA techniques, makes it possible to obtain an increased provision of Ery4P and, as a consequence, an improvement in the formation of L-tryptophan, L-tyrosine or L-phenylalanine as products. Both Draths K. M. et al. (J. Am. Chem. Soc. 114 (1992) 3956–62) and Flores N. et al. (Nat. Biotechnol. 14 (1996) 620–3) demonstrated the same effect. However, as Feldmann has shown, simply increasing the activity of transketolase in *Zymomonas mobilis* strains lacking transaldolase activity leads to the enrichment of metabolites of the pentose phosphate pathway in the cells and, as a consequence, to negative effects on cell growth (Feldmann S. D. et al., Appl. Microbiol. Biotechnol. 38 (1992) 354–61). This physiological effect may possibly be attributable to an excessive intracellular concentration of sedoheptulose-7-phosphate. The inventors have also found a corresponding inhibition of biomass growth as a consequence of transketolase overexpression in the case of *E. coli* tal$^+$ strains.

The object of the invention is, therefore, to make available an alternative process for producing substances, in particular aromatic amino acids, which process is distinguished by an increased provision of intracellular metabolic intermediates for the synthesis of these substances without suffering from the above-cited disadvantages of the processes, which disadvantages are the consequence of only increasing the activity of the transketolase.

Surprisingly, this object is achieved, according to the invention, by making available a process for the microbial preparation of substances, in which process the activity of a transaldolase is increased in a microorganism which is producing these substances, with the activity of a phosphoenolpyruvate (PEP)-dependent sugar-uptake system in this microorganism being present, reduced or absent.

This result is particularly surprising in that it is in no way self-evident that transaldolases play an important role in the growth of microorganisms and in their production of substances. This particularly applies in the case of growth on hexoses. Thus, yeast strains are known, for example, which are still able to grow on glucose despite having a mutation in the transaldolase gene (Schaaff L. et al., Eur. J. Biochem. 188 (1990) 597–603). Accordingly, a transaldolase should not exert any essential influence on cell growth. This is supported by the fact that bacterial species are also known which are able to grow in the absence of a transaldolase (Feldmann S. D. et al., Appl. Microbiol. Biotechnol. 38 (1992) 354–62).

In addition, hexoses such as glucose, in contrast to xylose and other pentoses, can also be metabolized through degradation pathways other than the pentose phosphate pathway. It is therefore in no way self-evident that transaldolase has an essential function in glucose degradation.

It may also be noted that an increased flow by way of the enzymes of the pentose phosphate pathway was measured in vitro in extracts of *Saccharomyces cerevisiae* cells in which the activity of a transaldolase was increased (Senac T. et al., Appl. Environ. Microbiol. 57 (1991) 1701–6). However, the experimental conditions which were selected in this study do not permit any transfer of the results to the natural phenomena of metabolic physiology which occur in living microorganisms, in particular bacteria. In addition, it may be noted that Liao J. C. et al. (Biotechn. Bioeng. 52 (1996) 129–140 have shown that when the activities of a transaldolase and AroG are simultaneously increased, DAHP formation increases. This effect is to be ascribed mainly to the increase in AroG activity. An increase in the production of substances as a result of an increase in transaldolase activity as such is not disclosed or indicated. It is therefore in no way to be expected that there is a causal relationship between an increase in transaldolase activity in microorganisms and the provision of Ery4P for the improved production of substances. Increasing the activity (overexpression) of a transaldolase in accordance with the present invention makes available an alternative process for implementing an increased flow of carbon through the pentose phosphate pathway and consequently effecting an improved provision of the primary metabolite Ery4P. An increased quantity of Ery4P is consequently available for the microbial synthesis of substances in whose synthesis at least one intermediate of the pentose phosphate pathway, and in particular Ery4P, is involved. The inventors have shown that the improved availability of Ery4P occurs both in microorganisms in which the activity of a PEP-dependent sugar-uptake system is present or reduced and in microorganisms in which such an activity is absent. Thus, according to the invention not only organisms which still have active phosphotransferase systems (PTS) or phosphotransferase systems with reduced activity (pts$^+$ strains) may be used but also organisms in which the PTS has been switched off (pts$^-$ strains).

Within the meaning of the invention, substances are to be understood as being, for example, fine chemicals such as aromatic amino acids, indigo, indoleacetic acid, adipic acid, melanin, quinones and benzoic acid, and also their potential derivatives and secondary products—or, in a general manner, secondary products of intermediates of the pentose phosphate pathway. However, this should also include all the compounds, for example pyridoxine and its derivatives, whose biochemical synthesis is promoted by the provision of erythrose 4-phosphate. Within the context of this invention, all these substances are also regarded as being substances from aromatic metabolism. It may be noted in this context that further genetic alterations to the substance-producing microorganisms are required, in addition to the novel interventions, for preparing indigo, adipic acid and other unnatural secondary products. The process according to the invention is particularly suitable for the preparation of substances in microorganisms which have not, prior to the increasing of the transaldolase activity, been selected as strains with a switched-off phosphotransferase system (pts$^-$ strains) from strains which previously harboured a phosphotransferase system (pts$^+$ strains). In this connection it may be noted that the non-prepublished patent specification WO-96/34961 describes such a selection from what were previously pts$^+$ strains, but in this study this selection precedes the increasing of the transketolase or transaldolase activity.

With regard to increasing the activity of a transaldolase, preference is given to increasing the activity of an *Escherichia coli* transaldolase and, in particular, the activity of *Escherichia coli* transaldolase B (TalB). When the corresponding talB gene is used, this gene preferably originates from *Escherichia coli* K12 or from a strain which is derived therefrom. Besides this, however, any gene is also suitable whose gene product catalyses a reaction which corresponds to that of transaldolase, that is the conversion of sedoheptulose 7-phosphate plus glyceraldehyde 3-phosphate to Ery4P and fructose-6-phosphate.

In a particularly advantageous embodiment of the invention, the activity of a transketolase is increased in addition to increasing the activity of a transaldolase. In the presence of pentoses, the expression of a transketolase gene on its own leads to a build up of metabolites in the pentose phosphate pathway (Feldmann S. D., Appl. Microbiol. Biotechnol. 38 (1992) 354–61). This has a harmful effect on the cell and results, inter alia, in the transformed cells growing at a diminished rate. The inventors also observed an identical effect in the case of an *Escherichia coli* strain which was growing on glucose and which exhibited increased transketolase activity. However, simultaneously increasing the activity of a transketolase as well as that of a transaldolase has now been found to be very beneficial for providing Ery4P and does not exhibit the negative side effects of a sole overexpression of a transketolase. The accumulation of metabolites of the pentose phosphate pathway which occurs when the activity of a transketolase is increased consequently fails to materialize as a result of increasing the activity of a transaldolase, as the result of which the impairment in the growth of the cells is not only halted but even converted into an increase in growth. It turns out, therefore, that increasing the activity of a transketolase particularly in strains having an increased activity of transaldolase in accordance with the invention is a sensible measure.

With regard to increasing the activity of a transketolase, preference is given to increasing the activity of an *Escherichia coli* transketolase and, in particular, the activity of *Escherichia coli* transketolase A (TktA). When the corresponding tkta gene is used, this gene preferably originates from *Escherichia coli* K12 or from a strain which is derived therefrom. In addition to this, however, any gene is also suitable whose gene product catalyses a reaction which corresponds to that of transketolase, that is the conversion of ribose 5-phosphate plus xylulose 5-phosphate to sedoheptulose 7-phosphate plus glyceraldehyde 3-phosphate or the conversion of xylulose 5-phosphate plus Ery4P to fructose 6-phosphate plus glyceraldehyde 3-phosphate.

In another particularly preferred embodiment of the invention, the activity of a transport protein for the PEP-7independant uptake of a sugar and/or the activity of a kinase which phosphorylates the corresponding sugar is/are increased in addition to increasing the activity of a transaldolase or increasing the activity of a transaldolase and a transketolase. In the case of the transport protein, the activity of this protein is understood as being the protein-mediated uptake rate. The additional increase in the activity of one of these latter proteins, i.e. the transport protein and the kinase, or of both proteins makes it possible to achieve an even higher production of substances, in particular aromatic amino acids, due to the fact that PEP is provided in increased quantity for the condensation with Ery4P to form the primary metabolite of the general pathway for biosynthesizing aromatic compounds, i.e. deoxy-D-arabinoheptulosonate-7-phosphate (DAHP).

It is advisable to use a facilitator as the transport protein for the PEP-independent uptake of a sugar, that is a transport protein which acts in accordance with the principle of protein-mediated facilitated diffusion. In particular, it is suitable to use the glucose facilitator protein (Glf) from *Zymomonas mobilis*. When the latter is used, the protein-encoding gene, glf, is obtained, for example, from *Z. mobilis* ATCC 10988, ATCC 29191 or ATCC 31821. However, other bacterial sugar transport genes whose gene products transport glucose, fructose or sucrose, for example, and in doing so do not use any PEP, for example the GaIP system from *Escherichia coli*, are also suitable for the novel process. Genes for sugar transport systems, such as HXT1 to HXT7, from eukaryotic microorganisms, such as *Saccharomyces cerevisiae, Pichia stipitis* or *Kluyveromyces lactis*, or sugar transport genes from other organisms in general, can also be used, provided that they can be expressed in a functional manner in the microorganisms and that the gene products can, in this context, operate without using PEP for transporting the sugars. It is particularly advisable for it to be possible to express the sugar transport genes in amino acid-producing microorganisms (amino acid producers).

It is particularly suitable, therefore, to use the facilitator gene glf, isolated from Z. mobilis ATCC 31821, for taking up sugars such as glucose, fructose or mannose when preparing aromatic amino acids in accordance with the novel process. (Parker C. et al., Mol. Microbiol. 15 (1995) 795–802; Weisser P. et al., J. Bacteriol. 177 (1995) 3351–4). The process according to the invention is particularly suitable for the preparation of aromatic amino acids in microorganisms in which the PTS system has a reduced activity or is completely absent. In such cases the PTS system may be reduced or switched off before but also after the increasing of the transaldolase activity.

The glf gene, in particular, should preferably be inserted at a low gene copy number in order to avoid harmful effects on the cell due to excessive expression of membrane proteins. Thus, a gene copy number of from 2 to 5 is preferred, for example, for the glf gene. It is particularly advantageous to insert the glf gene into one of the genes of the ptsHI-crr operon, for example into the ptsI gene.

When a sugar-phosphorylating kinase is being employed, it is advisable to use a hexose-phosphorylating kinase, preferably a kinase, in particular glucokinase (Glk), from Zymomonas mobilis. When the latter is used, the protein-encoding gene, glk, is derived, for example, from Z. mobilis ATCC 10988, ATCC 29191 or ATCC 31821. Other genes for hexose-phosphorylating kinases from bacteria whose gene products phosphorylate hexoses while consuming ATP, such as a fructokinase or a mannokinase, are likewise suitable for the novel process. Furthermore, genes for, for example, kinases from eukaryotic microorganisms, such as Saccharomyces cerevisiae, or, in a general manner, genes for sugar-phosphorylating kinases from other organisms, are also suitable, provided they can be expressed in a functional manner in the microorganisms, in particular amino acid producers, and can operate without using PEP to phosphorylate the sugars. The glucokinase gene, glk, for phosphorylating glucose, which gene is isolated from Z. mobilis ATCC 29191, is particularly suitable for preparing aromatic amino acids in accordance with the novel process.

The availability of PEP for producing the first intermediate of aromatic amino acid metabolism can be limited in microorganisms in which the flow of material towards Ery4P is increased. In these cases, it can be advantageous to reduce, or completely switch off, other PEP-consuming reactions in the metabolism, such as the reaction of the PEP:sugar phosphotransferase system (PTS), which catalyses a PEP-dependent sugar uptake, if this system is present. According to the invention, use can be made both of organisms which still possess active PTS genes (pts$^+$ strains) and, for the further improvement of the process, of pts mutants in which the activity of the pts is decreased (also to be considered as pts$^+$ in the present case) or in which the pts is switched off (pts$^-$ strains). A decrease of this nature can either be effected at the enzymic level or by using genetic methods, for example by inserting a glf and/or a glk gene into the chromosome and, in particular, into the locus of the ptsI gene, a procedure which simultaneously stabilizes the recombinant DNA in the chromosome (segregation stability) and consequently means that the use of a vector can be dispensed with. The inventors' experiences have shown that reducing or switching off the activity of the PTS should preferably not take place before the activity of the transaldolase is increased.

Within the meaning of the invention, measures for increasing the activity are to be understood as being all measures which are suitable for increasing the activity of the transaldolase, of the transketolase, of the transport protein, and of the kinase. The following measures are particularly suitable for this purpose:

introduction of genes, for example using vectors or temperate phages;

increasing the gene copy number, for example using plasmids with the aim of introducing the genes according to the invention into the microorganism at an increased copy number, that is at a copy number which is slightly (e.g. from 2 to 5 times) increased to highly (e.g. from 15 to 50 times) increased;

increasing gene expression, for example by increasing the rate of transcription, for example by using promoter elements such as Ptac, Ptet or other regulatory nucleotide sequences, and/or by increasing the rate of translation, for example by using a consensus ribosome binding site;

increasing the endogenous activity of enzymes which are present, for example by means of mutations which are produced in a random manner by conventional methods, for example using UV irradiation or mutation-eliciting chemicals, or by means of mutations, such as deletion(s), insertion(s) and/or nucleotide exchangers), which are produced in a specific manner using genetic engineering methods;

increasing the activity of enzymes by altering the structure of enzymes, for example by means of mutagenesis using physical, chemical or molecular biological or other microbiological methods;

using deregulated enzymes, for example enzymes which are no longer subject to feedback inhibition;

introduction of corresponding genes which encode the deregulated enzymes.

Combinations of the abovementioned methods and other, analogous methods can also be employed for increasing the activity. The endogenous or introduced activity of transport proteins can be increased, for example, by cloning the gene using the abovementioned methods, for example, or by selecting mutants which exhibit an increased transport of substrates Preferably, the activity is increased by integrating the gene, or the genes, into a gene structure, or into several gene structures, with each gene or the genes being introduced into the gene structure as (a) single copy(ies) or at an increased copy number. Within the meaning of the invention, a gene structure is to be understood as being a gene and any other nucleotide sequence which carries the genes according to the invention. Appropriate nucleotide sequences can, for example, be plasmids, vectors, chromosomes, phages or other nucleotide sequences which are not closed circularly.

A chromosome within the meaning of the invention is a chromosome into which at least one gene according to the invention has been inserted, with the resulting nucleic acid sequence containing at least one gene, or one gene copy, more than is naturally contained in this chromosome. On the other hand, for example, homologous recombination within a gene locus leads to a chromosome which does not necessarily have to differ from the natural form. The chromosomes which are prepared by homologous recombination are not, therefore, to be regarded as being in accordance with the invention if the natural number of homologous genes is not exceeded.

Within the meaning of the invention, a gene structure is also to be understood as being a combination of the abovementioned gene carriers, such as vectors, chromosomes and temperate phages, on which the genes according to the invention are distributed. For example, two tal genes can be introduced into the cell on a vector or two tal genes can be inserted into a chromosome. In addition, a further gene can, for example, be introduced into the cell using a phage. The same applies to the other genes according to the invention. These examples are not intended to exclude other combinations of gene distributions from the invention. In any case, it is crucial that the number of genes contained in the microorganism according to the invention exceeds the natural number of the corresponding genes. Preferably, the number of glf genes, for example, will be increased by a factor of from 2 to 5 in order to achieve the increase in activity according to the invention No cell-toxic effect will appear at these concentrations. However, it is also conceivable to introduce the genes according to the invention into the microorganism at a higher copy number of up to 50 gene copies of a form having the same effect.

In the novel process for producing substances, preference is given to employing microorganisms in which one or more enzymes which are additionally involved in synthesizing the substances are deregulated and/or have an increased activity.

These enzymes are, in particular, the enzymes of aromatic amino acid metabolism and, especially, DAHP synthase, shikimate kinase and chorismate mutase/prephenate dehydratase, and also all the other enzymes which are involved in synthesizing intermediates of aromatic metabolism and their secondary products.

Apart from the enzymes according to the invention, the deregulation and overexpression of DAHP synthase in particular is of importance for preparing substances such as adipic acid, bile acid and quinone compounds and their derivatives. In addition, shikimate kinase should be deregulated, and its activity increased, in order to achieve superelevated synthesis of, for example, tryptophan, tyrosine, indigo and derivatives of hydroxybenzoic acid and aminobenzoic acid and naphthoquinones and anthroquinones and also their secondary products. Deregulated and overexpressed chorismate mutase/prephenate dehydratase is additionally of particular importance for efficiently producing phenylalanine and phenylpyruvic acid and their derivatives. However, this is also intended to encompass all the other enzymes whose activities contribute to the biochemical synthesis of substances, that is compounds whose production is promoted by the provision of erythrose 4-phosphate, for example pyridoxine and its derivatives. It may be noted that further genetic alterations to the substance-producing microorganisms, in addition to the novel interventions, are required for the purpose of preparing indigo, adipic acid and other unnatural secondary products.

The novel process is suitable, in particular, for preparing aromatic amino acids, in particular phenylalanine. In the latter case, the gene expression and/or the enzyme activity of a deregulated DAHP synthase (e.g. in *E. coli* AroF or AroH) and/or of a likewise deregulated chorismate mutase/ prephenate dehydratase (PheA) is preferably increased.

*Escherichia* species, and also microorganisms of the genera Serratia, Bacillus, Corynebacterium or Brevibacterium, and other strains which are known from conventional amino acid methods, are suitable for use as production organisms. *Escherichia coli* is particularly suitable.

Another object of the invention is to provide suitable gene structures, and transformed cells carrying these gene structures, which enable the process to be implemented in a particularly successful manner. Within the context of the invention, novel gene structures are now made available, which gene structures contain, in recombinant form, a) a gene encoding a transaldolase or a gene encoding a transaldolase and a gene encoding a transketolase, and b) at least one gene encoding a transport protein for the PEP-independent uptake of a sugar or encoding a kinase which phosphorylates a sugar. In these gene structures, it is preferred that the gene for the transport protein encode a facilitator and the gene for the kinase encode a hexose-phosphorylating kinase. In particular, the genes for the transaldolase and the transketolase are derived from *Escherichia coli* and the genes for the transport protein and the kinase are derived from *Zymomonas mobilis*.

Gene structures are particularly advantageous in which the gene for the transaldolase is *Escherichia coil* talB and the gene for the transketolase is *Escherichia coli* tktA, while the gene for the transport protein is *Zymomonas mobilis* glf and the gene for the kinase is *Zymomonas mobilis* glk.

The appropriate genes are isolated, and the cells are transformed, in accordance with current methods: the complete nucleotide sequences of the talB and tktA genes from *Escherichia coli* K12 areknown (Yura T. et al., Nucl. Acid Res. 20 (1992) 3305–8; Sprenger G. A., Biochim. Biophys. Acta 1216 (1993) 307–10; Sprenger G. A. et al., J. Bacteriol. 177 (1995) 5930–9) and deposited in databases such as that of the EMBL in Heidelberg. When the *Escherichia coil* talB gene is being cloned, the polymerase chain-reaction (PCR) method is suitable, for example, for specifically amplifying the gene using chromosomal DNA from *Escherichia coli* K12 strains (Sprenger G. A. et al., J. Bacteriol. 177 (1995) 5930–9). The homologous complementation of a transketolase-deficient mutant is suitable, for example, when cloning the *Escherichia coli* tkta gene (Sprenger G. A. in: Bisswanger H. et al., Biochemistry and physiology of thiamine diphosphate enzymes, VCH (1991) 322–6).

When cloning the *Zymomonas mobilis* transport gene glf or the *Zymomonas mobilis* glucokinase gene glk, for example, PCR, for example, is suitable for specifically amplifying the gene using chromosomal DNA from *Zymomonas mobilis* strains ATCC 29191 or ATCC 31821, as is also the heterologous complementation of *Escherichia coli* mutants which are defective in PTS functions and which are therefore unable to transport glucose, for example (Snoep J. L. et al., J. Bacteriol. 174 (1994) 1707–8; Parker C. et al., Mol. Microbiol. 15 (1995) 795–82; Weisser P. et al., J. Bacteriol. 177 (1995) 3351–4). After isolating the genes and recombining them in vitro with known low copy number vectors such as pACYC184, pACYC177, pSC101 or pZY507 (Weisser P. et al., J. Bacteriol. 177 (1995) 3351–4), the host cell is transformed using chemical methods, electroporation, conjugation or transduction.

The isolated transaldolase gene can be integrated, together with one or more of the genes described within the context of the invention, in any combination, into a gene structure or into several gene structures. Without considering the precise allocation to gene structures, this leads to combinations such as talB, talB+tktA, talB+glf, talb+glk, talb+glf+glk, talb+tkta+glf, talb+tkta+glk or talb+tktA+glf+ glk.

Gene structures are advantageous which contain at least one regulatory gene sequence which is assigned to one of the genes. Thus, reinforcement of regulatory elements can preferably be effected at the level of transcription by, in particular, reinforcing the transcription signals. This can be effected, for example, by increasing the activity of the promoter or the promoters by altering the promoter sequences which are located upstream of the structural genes or by completely replacing the promoters with more effective promoters. Transcription can also be reinforced by exerting an appropriate influence on a regulatory gene which is assigned to the genes; in addition to this, however, it is also possible to reinforce translation by, for example, improving the stability of the messenger RNA (mRNA).

The most suitable gene structures are those in which at least one of the described genes is incorporated such that it is under the control of an inducible promoter. When the genes are arranged on a gene structure according to the invention, a promoter can be located upstream of a gene or be located, as a common promoter, upstream of several genes, or use can be made of two opposed promoters between which the genes are arranged such that they are read off in opposite directions. In this context, the glf gene, for example, can be located downstream of a relatively weak promoter (e.g. Ptet) and other genes can be under the control of the tac promoter. One or more DNA sequences can be located upstream and/or downstream of the genes contained in a gene structure, with or without an upstream promoter or with or without an assigned regulatory gene. By means of using inducible promoter elements, e.g. lacI$^q$/Ptac, it is possible to switch on new functions (induction of enzyme synthesis), for example by adding chemical inducers such as iso-propylthiogalactoside (IPTG).

The object of the invention is also achieved by providing transformed cells which harbour a gene structure according to the invention in replicable form.

Within the meaning of the invention, a transformed cell is to be understood as being any microorganism which carries a gene structure according to the invention, which gene structure brings about the increased formation of substances in the cell. The host cells can be transformed by means of chemical methods (Hanahan D., J. Mol. Biol. 166 (1983) 557–580) and also by means of electroporation, conjugation or transduction.

For the transformation, it is advantageous to employ host cells in which one or more enzymes which are additionally involved in the synthesis of the substances are deregulated and/or have an increased activity. A microorganism strain, in particular *Escherichia coli*, which is producing an aromatic amino acid or another substance according to the invention is transformed with the gene structure which contains the relevant genes. For transforming with the gene structures, it is advantageous to employ host cells in which the activity of the PEP-dependent sugar uptake system, if present, is decreased or switched off.

In particular, transformed cells are provided which are able to produce an aromatic amino acid, with the aromatic amino acid preferably being L-phenylalanine.

Using the novel process, and the microorganism which has been transformed in accordance with the teaching of the invention, a broad spectrum of substrates can be employed for producing substances. Within the context of the invention, a process for the microbial preparation of substances is consequently also provided in which cells which have been transformed in accordance with the invention and in which a gene structure is present which contains at least one regulatory gene sequence which is assigned to one of the genes are cultured, with enzyme synthesis being induced in the microorganisms after at least 2 cell divisions (beginning of the exponential growth phase). Consequently, the production of the microorganisms can be increased independently of their growth.

In a particularly preferred embodiment of the novel process, transformed cells are employed which, in addition to the intermediates of the pentose phosphate pathway, also contain an increased availability of other metabolites of central metabolism. These metabolites include, for example, pyruvate from glycolysis or gluconeogenesis, or oxaloacetate from the citric acid cycle. Furthermore, the relevant compound, or its precursors, that is the precursors of pyruvate or of metabolites of the citric acid cycle, such as fumarate or malate, can be made available to the growing cells by feeding.

The invention is explained in more detail below with the aid of a few implementation examples. The following strains have been deposited at DSM under the terms of the Budapest treaty:

DSM 11210 *Escherichia coli* AT2471/pZYTT7tal
DSM 11209 *Escherichia coli* AT2471/pZY557tkttal
DSM 11206 *Escherichia coll* AT2471IGP704glfint PTS$^+$
DSM 11205 *Escherichia coli* AT2471glfint PTS$^-$ The host organism employed, i.e. AT2471, has been deposited by Taylor and Trotter (Bacteriol. Rev. 13 (1967) 332–353) in the CGSC under number 4510 and is freely accessible.

The characteristics and the provenance of all the microorganisms employed within the context of this patent application are described in detail in Table 1.

The text which follows is intended to indicate the materials and methods employed and to support the invention with experimental examples and comparative examples:

General Methods

In the genetic studies, strains of *E. coli* were, unless otherwise indicated, cultured on LB medium consisting of Difco bacto-tryptone (10 g·l$^{-1}$), Difco yeast extract (5 g·l$^{-1}$) and NaCl (10 g·l$^{-1}$). Depending on the resistance properties of the strains employed, carbenicillin (20–100 mg·l$^{-1}$) and/ or chloramphenicol (17–34 mg·l$^{-1}$) was/were added to the medium if necessary. For this, carbenicillin was first of all dissolved in water, and chloramphenicol in ethanol, and the solutions were added, after having been sterilized by filtration, to the previously autoclaved medium. Difco bacto-agar (1.5%) was added to the LB medium for preparing agar plates. Plasmid DNA was isolated from *E. coli* by means of alkaline lysis using a commercially available system (Quiagen, Hilden). Chromosomal DNA was isolated from *E. coli* and *Z. mobilis* as described by Chen and Kuo (Nucl. Acid Res. 21 (1993) 2260).

Restriction enzymes, DNA polymerase I, alkaline phosphatase, RNase and T4 DNA ligase were used in accordance with the producers' instructions (Boehringer, Mannheim, Germany or Promega, Heidelberg, Germany). For restriction analysis, the DNA fragments were fractionated in agarose gels (0.8%) and isolated from the agarose by means of extraction using a commercially available system (Jetsorb Genomed, Bad Oeynhausen, Germany).

For Southern analyses, chromosomal DNA (10 μg) was digested with restriction enzymes, size-fractionated by gel electrophoresis and transferred to a nylon membrane (Nytran 13, Schleicher and Schuell, Dassel, Germany) by means of vacuum-mediated diffusion (VacuGene System, Pharmacia, Freiburg, Germany). Appropriate DNA fragments were isolated, labelled with digoxigenin-dUTP and used as probes. Labelling, hybridization, washing procedures and detection were performed with the aid of a commercially available labelling and detection system (Boehringer, Mannheim, Germany).

For transformation, the cells were incubated at 37° C. and 200 rpm for 2.5–3 h in LB medium (5 ml tubes). At an optical density (620 nm) of approx. 0.4, the cells were centrifuged down and taken up in one tenth the volume of TSS (LB medium containing 10% (w/v) PEG 8000, 5% (v/v) DMSO and 50 MM $MgCl_2$). After a 30-minute incubation at 4° C. with from 0.1 to 100 ng of DNA, and subsequent incubation at 37° C. for 1 h, the cells were plated out on LB medium containing an appropriate antibiotic.

EXAMPLE 1

Preparation of pZY557tal, pBM20tal and pZY557tkttal as Prototypes of Plasmid-based Gene Structures According to the Invention, and of pZY557tkt Plasmid pZY507 (Weisser et al. 1995 J. Bacteriol 177: 3351–3345) was opened using the restriction enzymes BamHI and HindIII and the larger fragment (10.1 kB of DNA) was isolated. A part of the multiple cloning site was excised from vector pUCBM20 (Boehringer, Mannheim, Germany) using BamHI and HindIII and ligated to the large pZY507BamHI/HindIII fragment, resulting in vector pZY557, which is similar to vector pZY507 apart from the other restriction cleavage sites. The talB gene was amplified from vector pGSJ451 (Sprenger G. A. et al., J. Bacteriol. 177 (1995) 5930–36) by means of PCR. For this, use was made of oligonucleotide I: 5' CCGCAT GCTGTTTAAAGAGAAATA 3' (the base pairs which are underlined here correspond to base pairs 84 to 101 of the talB sequence from Sprenger G. A. et al., J. Bacteriol. 177 (1995) 5930–6), which was provided with a cleavage site for the restriction enzyme SphI, and of the commercially obtainable M13/pUC sequencing primer (No. 1010093, Boehringer Mannheim, Germany) as oligonucleotide II. The resulting amplified DNA fragment contains a cleavage site for SphI at each end and was cleaved with the restriction enzyme SphI. This fragment was then ligated to vectors pZY557 and pUCBM20, respectively, which vectors had also been linearized with SphI. The recombinant plasmids pZY557tal and pBM20tal, respectively, were obtained after transforming E. coli with the two ligation solutions and cloning the transformants. The tktA gene was amplified by PCR from the vector pGSJ427 (Sprenger G. A. et al., Eur. J. Biochem. 230 (1995) 525–32) with a cleavage site for the restriction enzyme NotI being inserted at the 5' end and a cleavage site for the enzyme SphI being inserted at the 3, end. Use was made in this case of oligonucleotides III: 5' TTAGCGGCCGCCCTTCATCATCCGATCT 3' (the base pairs which are underlined here correspond to base pairs 126 to 146 of the tktA sequence from Sprenger G. A., Biochim. Biophys. Acta. 1216 (1993) 307–10), which was provided with a cleavage site for the restriction enzyme NotI, and IV: 5' ATAGCATGCTAATTACAGCAGTTC 3' (the base pairs which are underlined here correspond to base pairs 2018 to 2036 of the tktA sequence from Sprenger G. A., Biochim. Biophys. Acta. 1216 (1993) 307–10), which was provided with a cleavage site for SphI. The resulting PCR fragment was cleaved with NotI and SphI and ligated into vector pZY557tkt, which had been treated in the same way, resulting in vector pZY557tkt. pZY557tkt was then opened with SphI and ligated to the SphI-cleaved PCR fragment containing talB. After transforming E. coli and cloning the transformants (see above), plasmids were obtained which contained the tktA gene and the talB gene oriented in the same direction downstream of the tac promoter and which were subsequently used as gene structure pZY557tkttal.

The resulting transformants were stored at –80° C. on LB medium in the form of glycerol cultures (30%). When needed, the glycerol cultures were thawed directly before use.

EXAMPLE 2

Effect of the Increased Activity of a Transaldolase on the Growth of Strains in Which Transketolase Activity is Also Increased The growth of the E. coli strains AT2471, AT2471/pZY557tkt, AT2471/pZT557tal and AT2471/pZY557tkttal on glucose was investigated in mineral medium. This consisted of Na citrate·$3H_2O$ (1.0 g·$l^{-1}$), $MgSO_4$·$7H_2O$ (0.3 g·$l^{-1}$), $KH_2PO_4$ (3.0 g·$l^{-1}$), $K_2HPO_4$ (12.0 g·$l^{-1}$), NaCl (0.1 g·$l^{-1}$), $(NH_4)_2SO_4$ (5.0 g·$l^{-1}$), $CaCl_2$·$2H_2O$ (15.0 mg·$l^{-1}$), $FeSO_4$·$7H_2O$ (0.75 g·$l^{-1}$) and L-tyrosine (0.04 g·$l^{-1}$). Additional minerals were added in the form of a trace element solution (1 ml·$l^{-1}$), which was composed of $Al_2(SO_4)_3$·$18H_2O$ (2.0 g·$l^{-1}$), $CoSO_4$·$6H_2O$ (0.7 g·$l^{-1}$), $CuSO_4$·$5H_2O$ (2.5 g·$l^{-1}$), $H_3BO_3$ (0.5 g·$l^{-1}$), $MnCl_2$·$4H_2O$ (20.0 g·$l^{-1}$), $Na_2MoO_4$·$2H_2O$ (3.0 g·$l^{-1}$), $NiSO_4$·$3H_2O$ (2.0 g·$l^{-1}$) and $ZnSO_4$·$7H_2O$ (15.0 g·$l^{-1}$). Vitamin B1 (5.0 mg·$l^{-1}$) was dissolved in water and added, after having been sterilized by filtration, to the medium after the latter had been autoclaved, as were carbenicillin and/or carbenicillin and chloramphenicol as the need arose. Glucose (30 g·$l^{-1}$) was autoclaved separately and likewise added to the medium after the latter had been autoclaved.

For the experiments, shaking flasks (1000 ml containing 100 ml of mineral medium) were inoculated with 2 ml of glycerol culture and incubated at 37° C. and 150 rpm for 72 h on an orbital shaker. After reaching an optical density (620 nm) of ≈1, the cells were induced by adding 15–100 µM IPTG. The optical density of the culture was measured at regular intervals up-to this point. Under the above-described conditions, the host organism E. coli AT2471 reached an optical density of 1.2 after 7.25 h. The increase in the activity of the transketolase in mutant AT2471/pZY557tkt led to a marked reduction in the rate of growth; while having an identical optical density at the beginning of the experiment, this strain only reached an optical density of 0.49 after 7.25 h. The growth-inhibiting effect is probably attributable to the synthesis of inhibitory concentrations of metabolic intermediates of the pentose phosphate pathway.

The increase in the activity of the transaldolase in mutant AT2471/pZY557tal also led to a marked reduction (almost as marked as in the case of the transketolase) in the growth rate; an optical density of 0.52 was reached after 7.25 h. It was possible to reach an optical density of 1.1 after 7.25 h by increasing the activity of the transaldolase in addition to that of the transketolase, as was effected in E. coli AT2471/pZY557tkttal. This result makes it clear that additionally increasing the activity of a transaldolase in a strain having an increased activity of transketolase cancels the negative effects of only increasing the activity of the transketolase and permits virtually uninhibited growth.

EXAMPLE 3

Determination of the Enzyme Activities of the Transaldolase

In order to determine the activity of the transaldolase, the cells of E. coli AT2471, AT2471/pZY507, AT2471/pZY557tal and AT2471/pZY557tkttal were cultured as described above with, however, 3-(morpholino)propane-sulphonic acid (MOPS, 16.7 g·$l^{-1}$) being added to the medium and the phosphate concentration being lowered to one tenth of the concentration which was employed in the growth experiments. In order to check the induction of the cells, parallel experimental mixtures were set up, one of which mixtures was induced by adding IPTG (20 µM) after 7 cell divisions (OD~1). 20 ml of culture broth were removed from all the mixtures directly before adding the inducer to the relevant flasks and 3 h after the time of induction and the cells were sedimented at 6000 g for 10 min at 4° C.

The harvested cells were washed in 50 mM glycylglycine buffer, pH 8.5, containing 1 nM dithiothreitol, 10 mM $MgCl_2$ and 0.5 mM thiamine diphosphate. The cells in the sediment were disrupted by ultrasonic treatment (Branson 250 Sonifier fitted with a microtip) in a sonication cycle of 25% and at an intensity of 40 watts for 4 min per ml of cell suspension. After centrifuging at 18,000 g for 30 min at 4° C., the supernatant (crude extract) was used for measuring the activity of the transaldolase.

The transaldolase activity in the crude extract was determined using an enzymic test which was optically coupled to the formation of NAD. For this, the crude extract was incubated in a total volume of 1 ml containing 0.8 mM fructose 6-phosphate, 4 mM erythrose 4-phosphate and 0.3 mM NADH in buffer (50 mM glycylglycine, pH 8.5, 1 mM dithiothreitol, 10 mM $MgCl_2$ and 0.5 mM thiamine diphosphate). The resulting glyceraldehyde 3-phosphate was reacted with the enzymes triosephosphate isomerase (9 U) and glycerol 3-phosphate dehydrogenase (3 U), which enzymes were also added, with the formation of NAD. The oxidation of NADH was monitored spectrophotometrically at 340 nm ($\epsilon=6.3 \cdot 10^3$ $l \cdot mol^{-1} \cdot cm^{-1}$), with the conversion of 1 µmol of NADH being equivalent to the consumption of 1 µmol of fructose 6-phosphate. The turnover of 1 µmol of NADH per min was defined as 1 U.

The protein concentration in crude extracts was determined as described by Bradford (Anal. Biochem. 72 (1976) 248–254) using a commercially available colour reagent. Bovine serum albumin was used as the standard.

Table 2 shows the results of the enzyme measurements when using the host strain *E. coli* AT2471 and its mutants which harbour one of the plasmids pZY557, pZY557tal or pZY557tkttal. At the time of induction, the host strain and the strain carrying the vector pZY557 were found to have a transketolase activity of about 0.65 U·(mg of protein)$^{-1}$. As shown for *E. coli* AT2471/pZY557, this value increased in three hours, as the result of physiological growth, to 0.8 U·(mg of protein)$^{-1}$. Due to the absence of the tal gene on the vector employed, it was not to be expected that the induction which was performed in this experiment would have any effect.

In parallel experimental mixtures, *E. coli* AT2471/pZY557tal was found to have transketolase activities of 0.53 and 0.61 U·(mg of protein)$^{-1}$, respectively, at the time of induction. While the value for the transaldolase activity increased in 3 h to only 0.6 U·(mg of protein)$^{-1}$ when the culture was not induced, the transaldolase activity achieved a value of 1.06 U·(mg of protein) as a result of induction. In other experimental mixtures, *E. coli* AT2471/pZY557tkttal was used in what were otherwise identical experiments; in this case, the transaldolase activity had increased in the first 3 h after inducing the cells from 0.8 to 1.16 U·(mg of protein)$^{-1}$, which corresponded to a doubling of the activity as compared with the corresponding experiments using the host strain.

EXAMPLE 4

Production of Substances Using Strains Which Exhibit an Increased Transketolase Activity in Addition to the Increased Transaldolase Activity The medium which was employed for the growth experiments was used for determining synthetic performance. The cultures of *E. coli* AT2471 and AT2471/pZY557tkttal were induced at an optical density of 1 and the period of culture was extended to 72 h. After 24 and 48 h, the pH of the cultures was measured and brought back to the starting value of 7.2, if required, by adding KOH (45%). In addition, samples (2 ml) were taken after 24, 48 and 72 h for determining the optical density as well as the concentrations of glucose and L-phenylalanine.

The phenylalanine concentration was determined by means of high pressure liquid chromatography (HPLC, Hewlett Packard, Munich, Germany) in combination with fluorescence detection (extinction 335 nm, emission 570 nm). A Nucleosil-120-8-C18 column (250·4.6 mm) was used as the solid phase; the column was eluted using a gradient (eluent A: 90% 50 mM phosphoric acid, 10% methanol, pH 2.5; eluent B: 20% 50 mM phosphoric acid, 80% methanol, pH 2.5; gradient: 0–8 min 100% A, 8–13 min 0% A, 13–19 min 100% A). The elution rate was set at 1.0 ml·min$^{-1}$; the column temperature was set at 40° C. Post-column derivatization was carried out using o-phthalic dialdehyde in a reaction capillary (14 m·0.35 mm) at room temperature. L-phenylalanine was found to have a retention time of 6.7 min under the conditions described.

Measurement of the glucose concentration with enzyme test strips (Diabur, Boehringer Mannheim, Germany) and, depending on the results, the subsequent addition of 2 ml of a concentrated glucose solution (500 g·l$^{-1}$) ensured that glucose limitation did not arise in the experimental mixtures. After an incubation time of 48 h, a (phenylalanine) index value of 119 was achieved after inducing the host strain *E. coli* AT2471; this compares with a phenylalanine value of 100 for the uninduced host strain. Simply introducing the plasmid pZY557tkttal into the host strain had the result of increasing this index value, describing the phenylalanine concentration, to 167 even without inducing the cells. As the experiments show, inducing the strain *E. coli* AT2471/pZY557tkttal resulted in a further increase to a value of 204. This corresponded to an increase of 71% as compared with the induced host strain.

This result demonstrates the positive effect according to the invention, which effect increases the synthesis of aromatic compounds, of additionally increasing the activity of a transketolase in strains which already have an increased transaldolase activity, or of additionally increasing the activity of the transaldolase in strains which already have an increased transketolase activity.

EXAMPLE 5

Production of Substances Using Strains Having an Increased Transaldolase Activity The mutant *E. coli* AT2471/pZY557tal was cultured in an experiment which was otherwise identical to that described in Example 4. After 48 h, induction of the strain resulted in a (phenylalanine) index value of 131, which compares with a phenylalanine value of 100 for the uninduced strain.

This result clearly demonstrates the positive effect which increasing the activity of a transaldolase exerts on the synthesis of aromatic substances, particularly after inducing in accordance with the invention.

EXAMPLE 6

Production of Substances Using PTS$^-$ Mutants in Which a PEP-Independent Sugar Uptake System is Being Expressed in Addition to There Being an Increased Transaldolase Activity, with the Transaldolase Activity Being Increased after the Introduction of the PEP-Independent Sugar-Uptake System.

The glf gene was obtained, as described by Weisser P. et al. (J. Bacteriol. 177 (1995) 3351–54) using PCR (Mullis K.

B. et al., Meth. Enzymol. 155 (1987) 335–50). The complete nucleotide sequence of this gene is available (Barnell W. O. et al., J. Bacteriol. 172 (1990) 7227–40). The glf gene was amplified using plasmid pZY600 as the template (Weisser P. et al., J. Bacteriol 177 (1995) 3351–4).

For the purpose of integrating the glf gene into genes which encode components of the *E. coli* PTS system, plasmid pPTS1 (see Table 1) was digested with BglII and treated with Klenow fragment. The unique cleavage site is located in the ptsI gene. The glf gene was isolated, as a BamHI-KpnI fragment, from plasmid pBM20glfglk and likewise treated with Klenow fragment. Clones carrying the glf in the same orientation as the ptsHI genes were obtained by blunt-end ligation. A 4.6 kb PsCI fragment carrying the 3' region of the ptsH gene and ptsI containing integrated glf and crr was obtained from the resulting plasmid pPTSglf. This fragment was ligated into the EcoRV cleavage site of vector pGP704. Since this vector is only able to replicate in λpir strains, the vector has been integrated into the chromosome by transformants which do not harbour this phage if these transformants are able to grow on carbenicillin. The integration was checked by Southern blot analysis (Miller V. L. et al., J. Bacteriol. 170 (1988) 2575–83). The resulting transformants contained the complete PTS genes in addition to the glf gene.

The vector moiety can be recombined out in a second homologous crossover, resulting in the loss of the carbenicillin resistance. Since, in this case, the pts genes are interrupted by the insertion of the glf gene, the PTS is not expressed in a functional manner in these mutants. The desired PTS$^-$ mutants were selected as follows: after subculturing the transformants, which were still PTS$^+$, several times on LB medium without antibiotics, aliquots of the cell suspension were plated out on LB plates containing 100 $\mu g \cdot l^{-1}$ phosphomycin. PTS$^-$ mutants are able to grow on these plates. Growing clones were streaked out on LB plates containing either phosphomycin or 20 $\mu g \cdot l^{-1}$ carbenicillin. Chromosomal DNA was isolated from clones which still exhibited growth on the phosphomycin plates but which were not able to grow on the carbenicillin plates. The integration of the glf gene into the genes which encode the PTS system was confirmed by Southern analysis. Corresponding mutants were identified as being phenotypically PTS-deficient. One clone was selected as the host organism *E. coli* AT2471glfintPTS$^-$ and used for the transformations (see above) with plasmid pZY557tal. Following the experimental conditions described for Examples 4 and 5, the PTS-negative mutant *E. coli* AT2471glfintPTS$^-$/pZY557tal, and the corresponding host strain AT2471glfintPTS$^-$, were in each case cultured in two parallel mixtures and the cells of one mixture in each case were induced after approx. 7 divisions.

The induction reduced the synthetic performance of the host strain, which initially had an index value of 100 without induction, down to a value of 56. By comparison, the induction increased the phenylalanine index value from 73 to 103, and consequently above the initial value for the host strain, in cultures of the transformed strain AT2471glfintPTS$^-$/pZY557tal.

This result demonstrates that simply increasing the transaldolase activity has a positive effect on the synthesis of phenylalanine even in those microorganisms in which the activity of the PTS system is diminished, or this system is completely switched off, and into which, at the same time, a PEP-independent sugar uptake system has been integrated.

EXAMPLE 7

Production of Substances Using PTS$^-$ Mutants in Which in Addition to an Increased Transaldolase Activity a PEP-Independent Sugar-Uptake System has been Expressed, With the Transaldolase Activity Being Increased Before the Introduction of the PEP-Independent Sugar-Uptake System

*E. coli* AT2471/pZY557tal was obtained as described in Example 1. Subsequently in this strain a glf gene was integrated into the genes which encode components of the PTS system of *E. coli*. This integration was carried out as described in Example 6. Using the experimental conditions described in Examples 4 and 5, these PTS-negative *E. coli* AT2471glfintPTS$^-$/pZY557tal mutants were cultured. It was found that the biosynthetic performance of the derived mutants corresponded to that of the strains described in Example 6.

EXAMPLE 8

Production of Substances in a Fermentation Vessel Using Strains Having an Increased Transaldolase Activity and Strains Having an Increased Transketolase Activity in Addition to Their Increased Transaldolase Activity The mutants *E. coli* AT2471, *E. coli* AT2471/pZY557tal and *E. coli* AT2471/pZY557tkttal were cultured in a fermentation vessel (reactor volume 15 l). To this end, two shaking flasks (2000 ml) with the mineral medium described in Example 2 (250 ml) were used for preculturing. In this process, the glucose concentration was reduced to 5.0 g·l$^{-1}$. The flasks were inoculated with 2 ml of glycerol culture and incubated on an orbital shaker at 37° C. and 150 rpm until an optical density (600 nm) of 3 was reached.

The precultures were used for inoculating 4.5 l of production medium. This contained MgSO$_4$.7H$_2$O (0.3 g·l$^{-1}$), KH$_2$PO$_4$ (3.0 g·l$^{-1}$), NaCl 0.1 (g·l$^{-1}$), (NH$_4$)$_2$SO$_4$ (5.0 g·l$^{-1}$). CaCl$_2$.2H$_2$O (15.0 mg·l$^{-1}$), FeSO$_4$.7H$_2$O (0.75 g·l$^{-1}$) and L-tyrosine (0.24 g·l$^{-1}$). Additional minerals were added in the form of a trace element solution (1.5 ml·l$^{-1}$), which was composed of Al$_2$(SO$_4$)$_3$.18H$_2$O (2.0 g·l$^{-1}$), CoSO$_4$.6H$_2$O (0.7 g·l$^{-1}$), CuSO$_4$.5H$_2$O (2.5 g·l$^{-1}$), H$_3$BO$_3$ (0.5 g·l$^{-1}$), MnCl$_2$.4H$_2$O (20.0 g·l$^{-1}$), Na$_2$MoO$_4$.2H$_2$O (3.0 g·l$^{-1}$), NiSO$_4$.3H$_2$O (2.0 g·l$^{-1}$) and ZnSO$_4$.7H$_2$O (15.0 g·l$^{-1}$). Vitamin B1 (75.0 mg·l$^{-1}$) was dissolved in water and added, after having been sterilized by filtration, to the medium after the latter had been autoclaved. Glucose (15 g·l$^{-1}$) was autoclaved separately and likewise added to the medium after the latter had been autoclaved. By adding NH$_4$OH (25%) the pH value in the medium was controlled at 7, the oxygen partial pressure being controlled at a value of 20% via the stirrer speed, the air volume fed and the pressure inside the fermentation vessel. By adding a glucose solution (700 g·l$^{-1}$) the glucose concentration in the culture medium was kept at values around 5 g·l$^{-1}$. Depending on the fermentation time, L-tyrosine was added to the glucose solution in variable concentrations in order to avoid L-tyrosine limitation.

In experiments in which cell induction was effected, this was done in accordance with the invention after 6 hours by adding 50 $\mu$M of IPTG. After an incubation time of 36 hours, a (phenylalanine) index value of 120 was achieved by simply introducing the pZY557tal plasmid; this compares with a (phenylalanine) index value of 100 for the uninduced host strain *E. coli* AT2471. By means of induction according to the invention this value could be raised further to 153. By introducing the pZY557tkttal plasmid alone and thus raising the transketolase activity in addition to the transaldolase activity, a (phenylalanine) index value of 130 could be achieved compared with the host strain. The experiments further showed that the induction of the strain *E. coli* AT2471/pZY557kttal enabled a further increase in the (phenylalanine) index value to 250. This corresponds to an increase of 92% compared with the uninduced strain.

This result shows that even in experiments carried out in fermentation vessels an increase in the synthesis of aromatic compounds can be achieved according to the invention by increasing the transaldolase activity as well as by increasing the transketolase activity in strains which already have an increased transaldolase activity.

TABLE 1

| Strains and plasmids | Genotype/ characteristics | Source or reference |
| --- | --- | --- |
| *E. coli* AT2471 | tyrA4, relA1, spoT1, thi-1 | Taylor and Trotter, Bacteriol. Rev. 13 (1967) 332–53 |
| *E. coli* SY327 | araD, Δ(lac-pro), Rif$^r$, recA56, λ-phage pir function | Miller et al., J. Bacteriol. 170 (1988) 2575–83 |
| *E. coli* CC118 | Δ(ara-leu), araD, ΔlacX74, galE, galK, phoA20, thi-1, rpsE, rpoB, argE (Am), recA1, λpir lysogen | Manoil et al., Proc. Natl. Acad. Sci USA 22 (1985) 8129–33 |
| PZY507 | Cm$^r$ | Weisser et al., J. Bacteriol 177 (1995) 3351–4 |
| pZY507glfglk | *Z. mobilis* glf and glk genes in p-ZY507 | Weisser et al., J. Bacteriol 177 (1995) 3351–4 |
| PZY557 | pZY507, multiple cloning site of pUCBM20, Cm$^r$ | Sprenger, unpublished |
| pZY557tkttal | *E. coli* tktA and talB genes in pZY557 | This patent application |
| pACYC184 | Cm$^r$, Tet$^r$ | Chang and Cohen, J. Bacteriol. 134 (1978) 1141–1156 |
| pDIA3206 | Ap$^r$, 11.5 kb insert from *E. coli* K12 chromosome including ptsHI-crr genes | DeReuse et al., J. Bacteriol. 170 (1988) 3827–37 |
| pPTS1 | pACYC184 containing a 4 kb ClaI fragment which contains the ptsHI and crr genes from pDIA3206; Cm$^r$ | Jahreis, Osnabruck university, unpublished |
| pGP704 | Amp$^r$ | Miller et al., J. Bacteriol. 170 (1988) 2575–83 |

TABLE 2

| | | Transaldolase activity/ U · (mg of protein)$^{-1}$ | |
| --- | --- | --- | --- |
| Microorganism | Time after induction/ h | without induction | with induction |
| *E. coli* AT2471/ | 0 | | 0.64 |
| *E. coli* AT2471/ pZY557 | 0 3 | | 0.65 0.80 |
| *E. coli* AT2471/ pZY557tal | 0 3 | 0.53 0.6 | 0.61 1.06 |
| *E. coli* AT2471/ pZY557tkttal | 0 3 | 0.70 0.45 | 0.80 1.16 |

What is claimed is:

1. A process for the microbial preparation of substances from aromatic metabolism, the substances being secondary products from the pentose phosphate pathway, comprising the steps of:
   (i) increasing the activity of a transaldolase in a microorganism having an active phosphotransferase system to a level of activity higher than that in *Escherichia coli* AT2471;
   (ii) producing one of said substances in the microorganism having increased transaldolase activity; and
   (iii) optionally, switching off the phosphotransferase system after transaldolase activity is increased.

2. The process accging to claim 1, wherein substances are prepared in whose synthesis at least one intermediate of the pentose phosphate pathway is involved.

3. The process accrding to claim 2, wherein the intermediate is erythrose-phosphate (Ery4P).

4. The process according to claim 1, wherein the transaldolase is an *Escherichia coli* transaldolase.

5. The process according to claim 1, wherein the tansaldolase is transaldolase B (TalB) from *Eschenchia coli*.

6. The process accoming to claim 1, wherein in step (i) additionally the activity of a transketolase is increased to a level of activity higher than that in *E. coli* AT2471.

7. The process acceding to claim 6, wherein the transketolase is an *Escherichia coli* transketolase.

8. The process according to claim 6, wherein the tranaketolase is transketolase A (TktA) from *Escherichia coli*.

9. The process according to ciaim 1, wherein in step (i) additionally the activity of a transport protein for phosphoenolpyruvate (PEP)-independent uptake of a sugar is increased to a level of activity higher than that in *E. coli* AT2471.

10. The process according to claim 1, wherein in step (i) additionally the activity of a kinase which phosphorylates a sugar which is taken up in an unphosphorylated form into the microorganism is increased to a level of activity higher than that in *E. coli* AT2471.

11. The process according to claim wherein 1, wherein step (i) additionally the activity of a transport protein for PEP-independent uptake of a sugar and the activity of a kinase which phosphoryates said sugar is increased to a level of activity higher than that in *E. coli* AT2471.

12. The process according to claim 9 or 11, wherein the transport protein is a facilitator.

13. The process according to claim 12, wherein the facilitator is the *Zymomonas mobilis* glucose facilitator protein (Glf).

14. The process according to claim 10 or 11, wherein the kinase is a hexose-phosphorylating kinase.

15. The process according to claim 14, wherein the kinase is derived from *Zymomonas mobilis*.

16. The process according to claim 15, wherein the kinase is *Zymomonas mobilis* glucokinase (Glk).

17. The process according to claim 1, wherein said increasing the activity of a transalodase enzyme and optionally in addition thereto the activity of at least one enzyme selected from the group consisting of tranketolase, transport protein and a hexose-phosphorylating kinase comprises at least one of the following steps:
   a) introducing gene(s) encoding said enzyme(s);
   b) increasing gene copy numbers of said enzyme(s);
   c) increasing expression of the gene(s) encoding said enzyme(s); and
   d) increasing endogenous activity of said enzyme(s).

18. The process according to claim 17, wherein the increase in the activity is achieved by integrating the gene or genes into a gene structure or into several gene structures with the gene or genes being introduced into the gene structure as (a) single copy(ies) or in increased copy number.

19. The prcoess according to claim 1, wherein a microorganism is employed in which one or more enzymes, which are additionally involved in the synthesis of the substances, are deregulated and/or exhibit increased activity.

20. The process according to claim 1, wherein the substance which is prepared is an aromatic amino acid.

21. The process according to claim 20, wherein the aromatic amino acid is L-phenylalanine.

22. The process according to claim 1, wherein the microorganism employed belongs to the genus Escherichia, Seurratia, Bacillus, Corynebacterium or Breibacterium.

23. The process according to claim 22, wherein the microorganism is *Escherichia coli*.

24. The process according to claim 1, wherein transformed cells harbouring in replicable form a gene structure containing, in recombinant form:
   a) a gene encoding a transaldolase or a gene encoding a transaldolase and a gene encoding a transketolase, and
   b) at least one gene encoding a transport protein for PEP-independent uptake of a sugar and encoding a hexose-phosphorylating kinase, containing at least one regulatory gene sequence which is assigned to one of the genes, wherein at least one of the genes in the gene structure is incorporated such that it is under the control of an inducible promoter, are cultured, wherein during the cultivation induction is effected after 2 cell divisions at the earliest and precursors of pyruvate or metabolites of the citric acid cycle are fed to the transformed cells.

25. The process according to claim 24, wherein transformed cells are obtained having increased availability of intermediates of the pentose phosphate pathway and also increased availability of other metabolites of central metabolism.

26. The process according to claim 17, wherein the enzymes are not subject to feedback inhibition.

* * * * *